(12) United States Patent
Tanaka

(10) Patent No.: US 6,305,536 B1
(45) Date of Patent: Oct. 23, 2001

(54) METHOD FOR COVERING A MOUTH INSERT PORTION OF AN INTRAORAL CAMERA WITH A FILM-MADE SHEATH AND THE COMBINATION THEREOF

(75) Inventor: Hiroyuki Tanaka, Yokohama (JP)

(73) Assignee: NIX Company Ltd., Tokyo (JP)

( * ) Notice: Subject to any disclaimer, the term of this patent is extended or adjusted under 35 U.S.C. 154(b) by 0 days.

(21) Appl. No.: 09/460,726

(22) Filed: Dec. 14, 1999

(30) Foreign Application Priority Data

Dec. 17, 1998 (JP) .................................... 10-377960

(51) Int. Cl.⁷ ............................. B65D 85/38; A61B 1/04
(52) U.S. Cl. ...................... 206/316.2; 206/363; 206/497; 433/29; 600/122
(58) Field of Search .................................. 206/63.5, 306, 206/363, 364, 497, 316.2; 433/29; 600/121, 133, 123

(56) References Cited

U.S. PATENT DOCUMENTS

| | | |
|---|---|---|
| 3,650,775 * | 3/1972 | Simon et al. ........................ 206/497 |
| 4,757,381 | 7/1988 | Cooper et al. . |
| 5,069,337 * | 12/1991 | Bala ..................................... 206/306 |
| 5,406,939 * | 4/1995 | Bala ..................................... 206/63.5 |
| 5,480,302 * | 1/1996 | Fife ..................................... 206/63.5 |
| 5,643,175 * | 7/1997 | Adair ................................... 600/133 |
| 5,795,632 * | 8/1998 | Buchalter ............................ 206/363 |

\* cited by examiner

*Primary Examiner*—Jim Foster
(74) *Attorney, Agent, or Firm*—Crowell & Moring LLP

(57) ABSTRACT

A film-made sheath is formed of a transparent film and a shrinkable film. These transparent and shrinkable films are in a contiguous relation and are adhered or fusion-bonded at edges thereof into sheath-shaped configurations. The transparent and shrinkable films may be dimensioned such that the sheath can accommodate therein a mouth insert portion of an intraoral camera. The mouth insert portion of the intraoral camera can be covered with the film-made sheath by inserting the mouth insert portion into the sheath such that a light-receiving portion of the intraoral camera is located on a side of the transparent film, and then heating the shrinkable film.

13 Claims, 2 Drawing Sheets

F I G. 1
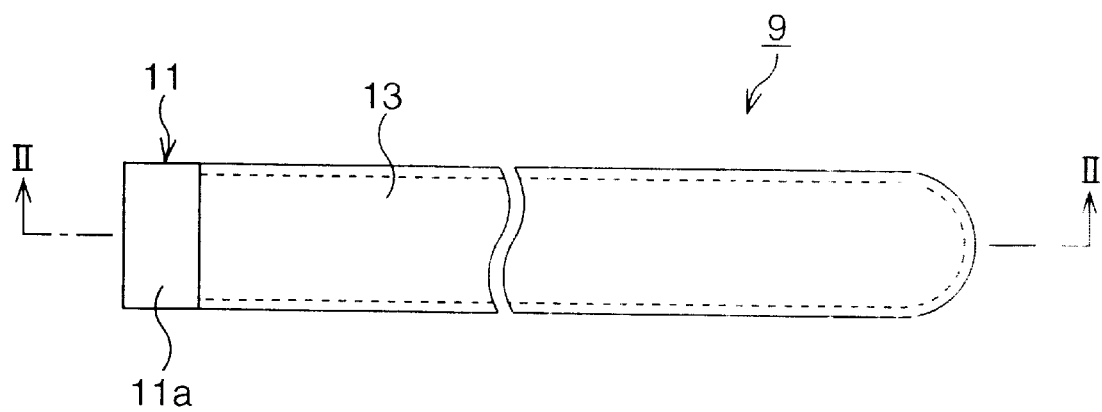
F I G. 2
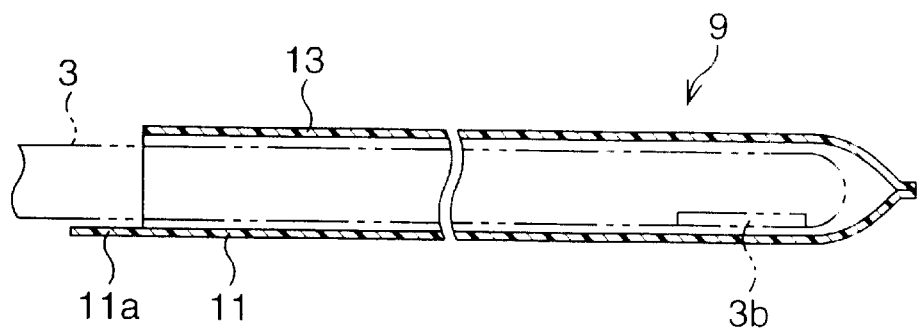

METHOD FOR COVERING A MOUTH INSERT PORTION OF AN INTRAORAL CAMERA WITH A FILM-MADE SHEATH AND THE COMBINATION THEREOF

BACKGROUND OF THE INVENTION a) Field of the Invention

This invention relates to a film-made sheath making use of a shrinkable film.

b) Description of the Related Art

In the dental care field, cameras which are useful ful for taking pictures inside oral cavities (hereinafter called "intraoral cameras") have been finding utility recently. FIG. 4 is a perspective view of an intraoral camera 1. The intraoral camera 1 is provided with a rod-shaped, mouth insert portion 3, a handle 5 and a cord 7. The mouth insert portion 3 is provided at a free end portion thereof with light portions 3a for illuminating an object to be imaged and also with a light-receiving portion 3b for receiving light from the object. The free end portion of the mouth insert portion 3 is inserted into the oral cavity of a patient. A particular part of the oral cavity, an image of which is desired, is illuminated by the light portions 3a, and light reflected from the particular part is received through the light-receiving portion 3b. The light so received is converted into video signals by CCD sensors or the like, and the video signals are transmitted to an external control box via the cord 7. At the control box, an image of the particular part is displayed on a monitor or the like for use in checking and/or treatment.

From the viewpoint of dental hygiene (specifically, the prevention of infectious diseases or the like), a film-made sheath formed of a transparent resin or the like is applied over the mouth insert portion 3. A new film-made sheath is applied whenever the intraoral camera is used for a different patient. For a conventional example, reference may be had to U.S. Pat. No. 4,757,381. Whenever such a conventional film-made sheath is used, it is, however, necessary to stretch the film-made sheath in a certain specific direction to avoid formation of wrinkles at a part of the film-made sheath, said part being brought into contact with the light-receiving portion 3b, because no good image would otherwise be available.

With the method that features the stretching of a film-made sheath in a certain specific direction as described above, wrinkles cannot be eliminated fully. To fully avoid formation of wrinkles, the film-made sheath has to be stretched in plural directions. This however requires both labor and time for applying the film-made sheath.

SUMMARY OF THE INVENTION

With the foregoing problem in view, the present invention has as a primary object thereof the provision of a film-made sheath which makes it possible to achieve wrinkle-free covering of an intraoral camera or the like without much labor and time.

To attain the above-described object, the present invention provides a film-made sheath comprising a transparent film and a shrinkable film. The transparent and shrinkable films are in a contiguous relation and adhered or fusion-bonded at edges thereof into sheath-shaped configurations.

Use of such a film-made sheath requires only insertion of an intraoral camera or the like into the sheath and subsequent heating of the shrinkable film. The intraoral camera can be easily covered without wrinkles.

The film-made sheath according to the present invention is usable not only for covering an intraoral camera or the like but also for other applications. For example, it can also be used to cover a mouth insert portion of a laser beam instrument for medical treatment or a free end portion of other mouth insert instrument (for example, a handpiece or the like).

According to the present invention, it is only necessary to apply the film-made sheath over an intraoral camera or the like and then to heat the shrinkable film. The covering of the intraoral camera or the like can be achieved extremely simply. As the shrinkable film undergoes shrinkage and as a result, stretches the transparent film, the transparent remains free of wrinkles. Formation of a finger grip on either the transparent film or the shrinkable film makes it possible to easily peel off the film-made sheath after use.

BRIEF DESCRIPTION OF THE DRAWINGS

FIG. 1 is a plan view of a film-made sheath according to an embodiment of the present invention;

FIG. 2 is a cross-sectional view of the film-made sheath, taken in the direction of arrows II—II of FIG.

DETAILED DESCRIPTION OF THE INVENTION AND PREFERRED EMBODIMENT

Figure 4:
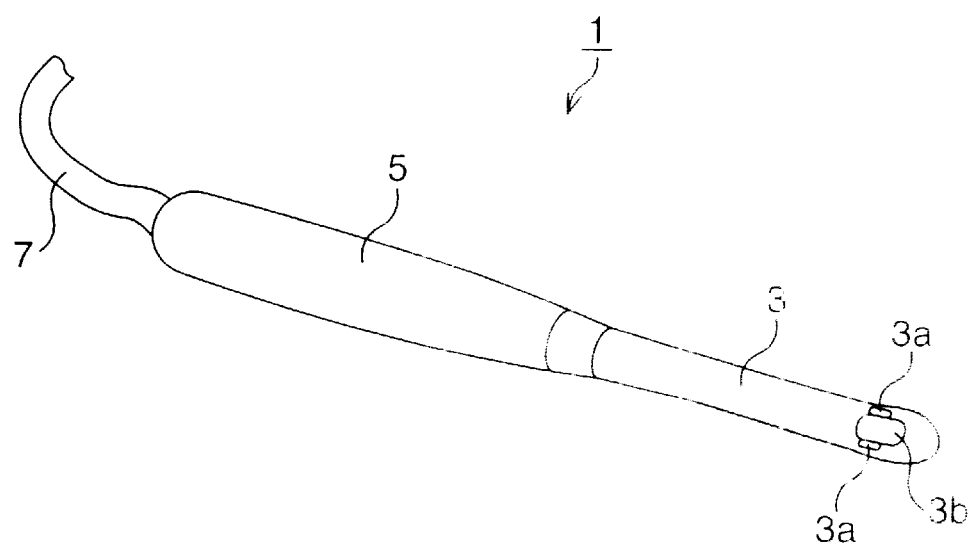
FIG. 4 is a perspective view of an intraoral camera.

Referring now to FIGS. 1 and 2, the film-made sheath according to the embodiment of the present invention will be described. The film-made sheath, which is generally designated by numeral 9, has been formed by bringing a transparent film 11 and a heat-shrinkable film 13 into a contiguous relation and then adhering (or fusion-bonding) them together at edge portions thereof as indicated by a dashed line in FIG. 1. Needless to say, to permit insertion of the mouth insert portion 3 of the intraoral camera 1 into the film-made sheath 9 (see FIG. 4), the adhesion (or fusion-bonding) is effected at and along the edge portions of the transparent film 11 and the heat-shrinkable film 13 except for parts of the edge portions. In the embodiment shown in FIG. 1, the transparent film 11 and the heat-shrinkable film 13 are not adhered (or fusion-bonded) at left-hand end portions thereof to define an opening through which the mouth insert portion 3 of the intraoral camera 1 can be inserted into the film-made sheath 9.

No particular limitation is imposed on the material of the transparent film 11, although a material having flexibility and low thermal deformability (i.e. shrink-resistant) is preferred. For example, PET, a polyester or the like can be used. Application of non-fogging treatment is preferred.

The transparent film 11 is formed a little longer than the shrinkable film 13 to form a finger grip 11a. Opposite to the embodiment shown in FIG. 1, the shrinkable film 13 may be formed longer. In essence, whichever film can be made longer than the other one insofar as the difference in length between both the films is sufficient to form the finger grip 11a.

No particular limitation is imposed on the material of the shrinkable film 13 insofar as it shrinks when heated. For example, a polyolefin film can be used. Further, the shrinkable film 13 can be either transparent or opaque (for example, colored).

As is illustrated by a phantom in FIG. 2, the mouth insert portion 3 of the intraoral camera 1 is inserted into the film-made sheath 9. At this time, the insertion should be conducted such that the light-receiving portion 3b is directed toward the transparent film 11.

With the mouth insert portion 3 inserted in the film made sheath 9 as illustrated in FIG. 2, the shrinkable film 13 is heated. As a heating method, it is possible to blow steam or hot air against the shrinkable film 13 or to pour hot water over the shrinkable film 13. Other conventional heating methods can also be used insofar as they conform with the object of the present invention. As a result of this heating, the shrinkable film 13 undergoes shrinkage. By this shrinkage, the film-made sheath 9 is brought into close contact with the mouth insert portion 3 of the intraoral camera 1.

Here, the transparent film 11 is in contact with the mouth insert portion 3 on the side of the light-receiving portion 3b, and the shrinkable film 13 is arranged on a side opposite to the light-receiving portion 3b. By the shrinkage of the shrinkable film 13, the transparent film 11 is stretched outwards at its periphery portions so that the transparent film 11 is evenly brought into contact with the light-receiving portion 3b. The transparent film 11 is therefore free of wrinkles over the light-receiving portion 3b. A good image can therefore be obtained.

After completion of the imaging, the transparent film 11 is pulled at the finger grip 11a in a direction away from the shrinkable film 13. As a result, the transparent film 11 is peeled off from the shrinkable film 13 and at the same time, is removed from the mouth insert portion 3 of the intraoral camera 1. This facilitates removal of the shrinkable film 13 from the mouth insert portion 3 of the intraoral camera 1. Although this finger grip 11a is not an essential element, its formation can facilitate removal of the film-made sheath after use. The film-made sheath can be easily replaced by a new one whenever an intraoral camera is applied to a different patient, and accordingly, is very hygienic and effective for the prevention of infection to bacteria or the like.

Figure 3:
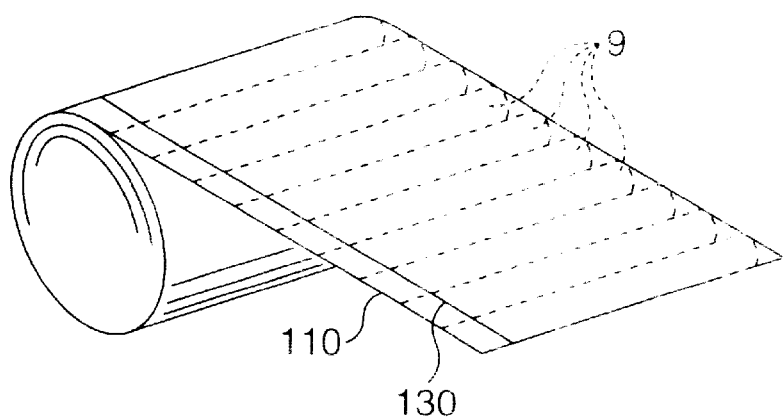
FIG. 3 is a perspective view of one example of continuously-formed, film-made sheaths.

With reference to FIG. 3, the continuously-formed, film-made sheaths will be described next. A number of film-made sheaths, each of which is of the same type as the film-made sheath according to the above-described embodiment, are formed side by side in the form of an elongated sheet. These film-made sheaths are torn off as many as needed. In FIG. 3, numeral 110 indicates a transparent film web while numeral 130 designates a shrinkable film web. Both sheets 110,130 are brought into a contiguous relation and are adhered (or fusion-bonded) into elongated envelops as indicated by dashed lines, whereby individual film-made sheaths 9 are formed. The elongated sheet made of both of the film webs combined together is formed into a roll as depicted in FIG. 3 and is supplied to a user. The individual film-made sheaths 9 are torn off along the adhered (or fusion-bonded) edges for use. If necessary, perforations may be formed through the adhered (or fusion-bonded) edges to facilitate the tearing.

This application claims the priority of Japanese Patent Application No. HEI 10-377960 filed Dec. 17, 1998, which is incorporated herein by reference.

What is claimed is:

1. In combination an intraoral camera and a film-made sheath, the film-made sheath covering a mouth insert portion of the intraoral camera, said film-made sheath comprising:

a shrink-resistant transparent film to be located on a side of a light-receiving portion of the mouth insert portion, and a shrinkable film to be located on a side opposite to the light-receiving portion, said transparent and shrinkable films being in a contiguous relationship and adhered or fusion-bonded at edges thereof into a sheath-shaped configuration having a non-sealing opening at one end of the sheath.

2. A method for covering a mouth insert portion of an intraoral camera with a film-made sheath, the film-made sheath comprising a shrink-resistant transparent film and a shrinkable film, said transparent and shrinkable films being in a contiguous relationship and adhered or fusion-bonded at edges thereof into a sheath-shaped configuration having a non-sealing opening at one end of the sheath, the method comprising:

inserting said mouth insert portion of said intraoral camera into said sheath such that a light-receiving portion of said intraoral camera is located on a side of said transparent film; and heating said shrinkable film to cover said mouth insert portion of said intraoral camera.

3. The method according to claim 2, wherein said transparent and shrinkable films are formed in elongated shapes and have different lengths in a longitudinal direction.

4. The method according to claim 2, further including subjecting said transparent film to a non-fogging treatment.

5. The method according to claim 3, wherein said transparent film is longer than the shrinkable film such that a portion of the transparent film forms a finger grip.

6. The method according to claim 2, wherein said transparent film is made from polyethylene terephthalate (PET).

7. The method according to claim 2, wherein said transparent film is made from polyester.

8. The method according to claim 2, wherein said transparent film is subjected to a non-fogging treatment.

9. The method according to claim 2, wherein said shrinkable film is made from polyolefin.

10. The method according to claim 2, wherein said shrinkable film is transparent.

11. The method according to claim 2, wherein said shrinkable film is opaque.

12. The method according to claim 2, wherein said shrinkable film is colored.

13. The method according to claim 3, wherein said shrinkable film is longer than the transparent film such that a portion of the shrinkable film forms a finger grip.

* * * * *